(12) United States Patent
Shimojo et al.

(10) Patent No.: US 6,316,473 B1
(45) Date of Patent: *Nov. 13, 2001

(54) TWO SURFACTANT-CONTAINING MEDICINAL COMPOSITION

(75) Inventors: Fumio Shimojo; Sumihisa Kimura, both of Kawanishi; Takeo Hirose, Kyoto; Satoshi Ueda, Kawanishi; Rinta Ibuki; Norio Ohnishi, both of Kyoto, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,469

(22) PCT Filed: Apr. 7, 1998

(86) PCT No.: PCT/JP98/01585

§ 371 Date: Oct. 12, 1999

§ 102(e) Date: Oct. 12, 1999

(87) PCT Pub. No.: WO98/46268

PCT Pub. Date: Oct. 22, 1998

(30) Foreign Application Priority Data

Apr. 11, 1997 (JP) ........................................ 9-93715

(51) Int. Cl.⁷ .................................................... A61K 31/40

(52) U.S. Cl. .......................... 514/336; 514/423; 514/428; 514/422

(58) Field of Search ..................................... 514/336, 361, 514/422, 428, 423

(56) References Cited

U.S. PATENT DOCUMENTS

| | | |
|---|---|---|
| 4,916,138 | 4/1990 | Ueda et al. . |
| 5,368,865 | 11/1994 | Asakura et al. . |
| 5,540,931 * | 7/1996 | Hewitt et al. .......................... 424/434 |

FOREIGN PATENT DOCUMENTS

| | | | |
|---|---|---|---|
| 423714 | * | 4/1991 | (EP) . |
| 428169 | * | 5/1991 | (EP) . |
| 2315216 | * | 1/1998 | (GB) . |
| 9501785 | * | 1/1995 | (WO) . |
| 9506464 | * | 3/1995 | (WO) . |
| 9613273 | * | 5/1996 | (WO) . |

* cited by examiner

*Primary Examiner*—William R. A. Jarvis
*Assistant Examiner*—Vickie Kim
(74) *Attorney, Agent, or Firm*—Oblon, Spivak, McLelland, Maier & Neustadt, P.C.

(57) ABSTRACT

Provided is a medicinal composition having a very satisfactory drug release profile and a very satisfactory drug absorption profile after oral administration characterized by its comprising an insoluble drug and two or more surfactants, at least one of the surfactants having as dissolved therein the insoluble drug and the other surfactant or surfactants.

4 Claims, No Drawings

TWO SURFACTANT-CONTAINING MEDICINAL COMPOSITION

TECHNICAL FIELD

This invention relates to a medicinal composition comprising a sparingly water-soluble medicinal substance and two or more surfactants and expressing very satisfactory release and oral absorption characteristics. The medicinal composition of this instant invention finds application in the field of medical care.

BACKGROUND ART

To provide a medicinal preparation of a medicinal substance which is only sparingly soluble in water (hereinafter referred to briefly as an insoluble drug), particularly such a preparation for oral administration, it is common practice to prepare a solid dispersion by mix-crystallizing a polymer such as hydroxypropylmethyl cellulose and the drug. By way of illustration, such a solid dispersion has been provided for the following FK506 (or FR-900506) Substance which, as is well known, has excellent immunosuppressant activity but is only sparingly soluble in water [Kokai Tokkyo Koho S62-277321].

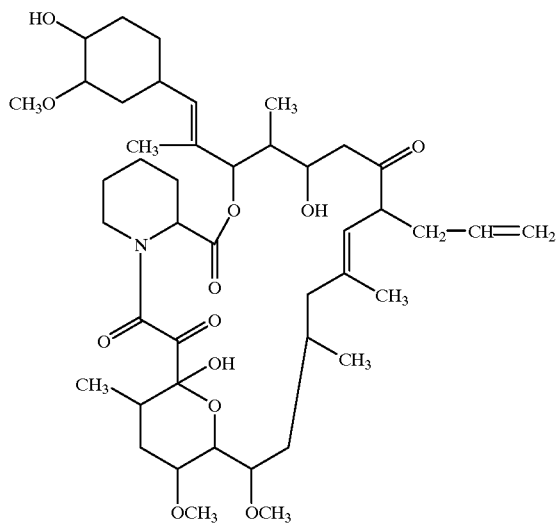

Generic name: tacrolimus

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0 4,9]octacos-18-ene-2,3,10,16-tetraone However, it is generally acknowledged that the oral absorbability of solid dispersions such as the above tends to vary rather appreciably.

After intensive investigations, the inventors of this invention have created a medicinal composition which, even when its active ingredient is an only sparingly water-soluble medicinal substance (insoluble drug), shows a very satisfactory drug release profile plus high oral absorption efficiency and absorbability with little variation.

DISCLOSURE OF INVENTION

This invention is essentially directed to a medicinal composition comprising an insoluble drug and two or more surfactants, at least one of said two or more surfactants having as dissolved therein the insoluble drug and the other surfactant or surfactants and to a process for producing said composition. This invention is now described in detail.

The "insoluble drug" to which the medicinal composition of this invention can be applied with advantage may be any pharmaceutical substance (drug) that is only sparingly soluble in water and includes, among others, the following tricyclic compound (I), which is represented by said FK506 Substance, and its pharmaceutically acceptable salt.

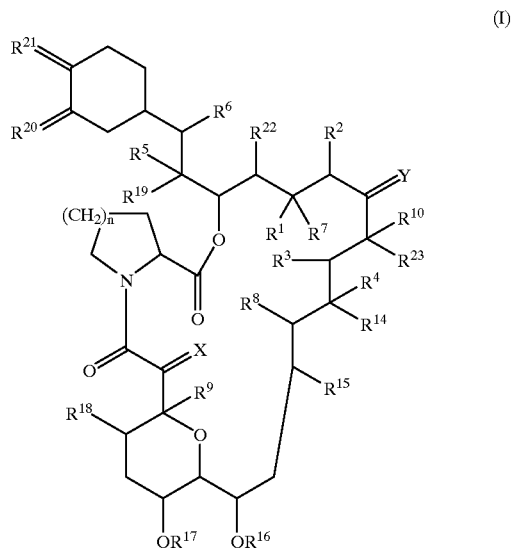

(I)

(wherein each of adjacent pairs of $R^1$ and $R^2$, $R^3$ and $R^4$ or $R^5$ and $R^6$ independently (a) is two adjacent hydrogen atoms, or
(b) may form another bond formed between the carbon atoms to which they are attached, and further, $R^2$ may be an alkyl group; $R^7$ is a hydrogen atom, a hydroxy group, a protected hydroxy group or an alkoxy group, or an oxo group together with $R^1$;

each of $R^8$ and $R^9$ is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;

X is an oxo group, (a hydrogen atom and a hydroxy group), (a hydrogen atom and a hydrogen atom), or a group represented by the formula —$CH_2O$—;

Y is an oxo group, (a hydrogen atom and a hydroxy group), (a hydrogen atom and a hydrogen atom), or a group represented by the formula N—$NR^{11}R^{12}$ or N—$OR^{13}$;

each of $R^{11}$ and $R^{12}$ is independently a hydrogen atom, an alkyl group, an aryl group or a tosyl group;

each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;

each of $R^{20}$ and $R^{21}$ is independently an oxo group or ($R^{20}$a and a hydrogen atom) or ($R^{21}$a and a hydrogen atom) in which each of $R^{20}$a and $R^{21}$a is independently a hydroxy group, an alkoxy group or a group represented by the formula —$OCH_2OCH_2CH_2OCH_3$, or $R^{21}$a is a protected hydroxy group, or $R^{20}$a and $R^{21}$a may together represent an oxygen atom in an epoxide ring;

n is an integer of 1 or 2; and
in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl and a group of the formula —$CH_2Se$ ($C_6H_5$)).

The compound (I) and its pharmaceutically acceptable salt are known as immunosuppressants (Japanese Tokkyo Kokai Koho S61-148181, EP 0323042), and FK506, in particular, has already been put to use in the therapy and prophylaxis of rejection reactions by transplantation of organs such as the heart, liver, kidney, bone marrow, skin, cornea, lung, pancreas, small intestine, muscle, nerve, limb, etc. and of various autoimmune diseases.

The above-mentioned compound (I) and its pharmaceutically acceptable salt can be provided by the same methods as disclosed in the two patent gazettes mentioned above. Particularly the tricyclic compounds produced by cultivation of *Streptomyces tsukubaensis* No. 9993 (FERM-BP 927) [deposited with National Institute of Bioscience and Human Technology Agency of Industrial Science and Technology (formerly Fermentation Research Institute Agency of Industrial Science and Technology), at 1-3, Higashi 1-chome, Tsukuba-shi, Ibaraki, Japan, date of deposit Oct. 5, 1984] or *Streptomyces hygroscopicus* subsp. *yakushimaensis* No. 7238 (FERM BP-928) [deposited with National Institute of Bioscience and Human Technology Agency of Industrial Science and Technology (date of deposit Jan. 12, 1985)] have been given the identification numbers FR-900506, FR-900520, FR-900523, and FR-900525 (Japanese Tokkyo Kokai Koho S61-148181).

First, the definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" are 1-(lowerlkylthio) (lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenyl-silyl, etc.), more preferably tri($C_1$–$C_4$) alkylsilyl group and $C_1$–$C_4$ alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, arboxyhexanoyl, etc.;

a cyclo (lower) alkoxy (lower) alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy (lower) alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower) alkylsilyl (lower) alkoxycarbonyl (lower) alk ylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, tri-methylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar (lower) alkanoyl group optionally having one or more suitable substituents such as lower alkoxy or trihalo (lower) alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy ($C_1$–$C_4$)alkanoyl group having two ($C_1$–$C_4$)alkyls at the cycloalkyl moiety, camphorsulfonyl group, carboxy-($C_1$–$C_4$)alkylcarbamoyl group, tri($C_1$–$C_4$) alkylsilyl-($C_1$–$C_4$)alkoxycarbonyl($C_1$–$C_4$)alkylcarbamoyl group, benzoyl group optionally having one or two nitro groups, benzenesulfonyl group having halogen, or phenyl ($C_1$–$C_4$)alkanoyl group having $C_1$–$C_4$ alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The pharmaceutically acceptable salt of the compound (I) includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the compound (I), it is to be understood that there may be conformers and one or more stereoisomers such as optical and geometrical isomers due to asymmetric carbon atom(s) and double bond(s), and such conformers and isomers are also included within the scope of the present invention.

The compound of the formula (I) and its salt can be in the form of a solvate, which is included within the scope of the present invention. The solvate preferably include a hydrate and an ethanolate.

The preferred examples of the tricyclic compound (I) is the one, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

each of $R^{20}$ and $R^{21}$ is independently ($R^{20}$a and a hydrogen atom) or ($R^{21}$a and a hydrogen atom) in which each of $R^{20}$a and $R^{21}$a is a hydroxy group or an alkoxy group, or $R^{21}$a is a protected hydroxy group; and n is an integer of 1 or 2. FK506 is the most preferable compound belonging to the tricyclic compound (I).

Other preferable compounds are listed hereinbelow.

1,14-Dihydroxy-12-[2-(4-hydroxy-3-methoxycyclohexyl)-1-methylvinyl]-23,25-dimethoxy-13,17,19,21,27-pentamethyl-11,28-dioxa-4-azatricyclo[22.3.1.0$^{4,9}$]octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$^{4,9}$] octacos-18-ene-2,3,10,16-tetraone, 17-allyl-1,14-dihydroxy-23,25-dimethoxy-13,19,21,27-tetramethyl-12-[2-[4-(3,5-dinitrobenzoyloxy)-3-methoxycyclo-hexyl]-1-methylvinyl]-11,28-dioxa-4-azatricyclo[22.3.1.0$^{4,9}$]-octacos-18-ene-2,3,10,16-tetraone, 17-allyl-12-[2-[4-[(−)-2-trifluoromethyl-2-methoxy-2-phenylacetoxy]-3-methoxycyclohexyl]-1-methylvinyl]-1,14-dihydroxy-23,25-dimethoxy-13,19, 21,27-tetramethyl-11,28-dioxa-4-azatricyclo[22.3.1.0$^{4,}$ $_9$]octacos-18-ene-2,3,10,16-tetraone.

17-ethyl-1,14-dihydroxy-12-[2-(4-hydroxy-3-methoxycyclo-hexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR900520), and 17-ethyl-1,14,20-trihydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone.

The surfactants for use in this invention are now described.

While two or more surfactants are used in the practice of this invention, such two or more surfactants can be judiciously selected from among pharmaceutically acceptable surfactants, whether naturally-occurring or synthetic. As regards natural surfactants, various surfactants of the animal origin or the vegetable origin can be selectively employed. Synthetic surfactants can also be used regardless of whether they are cationic, anionic or nonionic.

Of the two or more surfactants for use in this invention, at least one surfactant should be a liquid surfactant capable of dissolving not only the insoluble drug but also the other surfactant or surfactants and, as such, one or more species can be selected from among the following surfactants.

Propylene Glycol Mono- or Di-fatty Acid Esters

[propylene glycolmonocaprylate (e.g. Sefsol™-218), propylene glycol dicaprylate (e.g. Sefsol™-228), propylene glycol monocaprate, propylene glycol dicaprate (e.g. Sefsol™-220), propylene glycol monolaurate, propylene glycol monoisooctanoate (e.g. Sefsol™-2126), propylene glycol diisooctanoate (e.g. Sefsol™-2226), Migyol™ 840, etc.]

Fatty Acids

[oleic acid, linoleic acid, etc.]

Monohydric Alcohol Fatty Acid Esters

[isopropyl myristate, butyl myristate, isocetyl myristate, octyldodecyl myristate, isopropyl palmitate, isostearyl palmitate, isopropyl isostearate, isocetyl isostearate, butyl stearate, isocetyl stearate, cetyl isooctanoate, ethyl linoleate, isopropyl linoleate, hexyl laurate, ethyl oleate, decyl oleate, oleyl oleate, octyldodecyl myristate, hexyldecyl dimethyloctanoate, octyldodecyl neodecanoate, etc.]

Ethylene Glycol Fatty Acid Esters

[ethylene glycol mnonocaprylate (e.g. Sefsol™-118), ethylene glycol dicaprylate (e.g. Sefsol™128), ethylene glycol monoisooctanoate (e.g. Sefsol™-1126), ethylene glycol diisooctanoate (e.g. Sefsol™-1226), etc.]

Other Polyhydric Alcohol Fatty Acid Esters

[tetraglycerin monocaprylate (e.g. Sefsol™-618), tetraglycerin hexacaprylate (e.g. Sefsol™-668), etc.]

Dibasic Acid Diesters

[diisopropyl adipate, diisobutyl adipate, diethyl sebacate, diisopropyl sebacate, diethyl phthalate, etc.]

Alcohols

[oleyl alcohol, cetanol, stearyl alcohol, etc.]

Others [squalane, squalene, etc.]

Preferred are propylene glycol mono- or di-fatty acid esters and the more preferred is propylene glycol monocaprylate.

The other surfactant or surfactants, of said two or more surfactants, can also be selected from among the surfactants mentioned above but one or more species can be selected from among the following surfactants, for instance.

Polyoxyethylene Alkyl Ethers

[polyoxyethylene oleyl ether, polyoxyethylene stearyl ether, polyoxyethylene cetyl ether, polyoxyethylene lauryl ether (lauromacrogol J.P.), etc.]

Polyoxyethylene Sorbitan Fatty Acid Esters

[Tween™ 20, Tween™ 40, Tween™ 60, Tween™ 65, Tween™ 80, etc.]

Polyoxyethylene Glyceryl Mono-fatty Acid Esters

[polyoxyethylene glycerin monostearate etc.]

Polyoxyethylene propylene glycol mono-fatty acid esters

[polyoxyethylene propylene glycol monostearate, polyoxyethylene propylene glycol monooleate, etc.]

Polyoxyethylene Sorbitol Fatty Acid Esters
[polyoxyethylene sorbitol tetraoleate, polyoxyethylene sorbitol hexastearate, polyoxyethylene sorbitol monolaurate, polyoxyethylene sorbitol beeswax, etc.]

Polyoxyethylene Derivatives of Natural Oils or Waxes
[polyoxyethylene castor oil, polyoxyethylene hydrogenated castor oil (trademarks: HCO-40, HCO-60, Cremophore RH40, Cremophore RH60, etc.), polyoxyethylene lanolin, etc.]

Polyethylene Glycol Fatty Acid Esters
[polyethylene glycol monooleate, polyethylene glycol monostearate (e.g. polyoxyl stearate 40, J.P.), polyethylene glycol monolaurate, etc.]

Sorbitan Fatty Acid Esters
[sorbitan monooleate (e.g. Span™ 80), sorbitan monostearate (e.g. Span™ 60), sorbitan monopalmitate (e.g. Span™ 40), sorbitan monolaurate (e.g. Span™ 20), sorbitan monocaprylate (e.g. Sefsol™-418), etc.]

Sucrose Fatty Acid Esters
[DK-SS, DK-F160, DK-F140, DK-F110 (TM owned by Daiichi Kogyo Seiyaku), etc.]

Polyoxyethylene-polyoxypropylene Copolymer and Block Copolymer Surfactants
[Pluronic™ F87, Pluronic™ F127, Pluronic™ F68, Pluronic™ L44, Pluronic™ P123, Pluronic™ P85, Poloxamer™ 188, Poloxamer™ 235, Poloxamer™ 403, Poloxamer™ 407, etc.]

Alkyl Sulfate Salts
[sodium lauryl sulfate etc.]

Phospholipids
[purified egg yolk lecithin, purified soybean lecithin, etc.]

Bile Acid Salts
[sodium taurocholate, sodium glycocholate, etc.]

Preferred are polyoxyethylene derivatives and the more preferred is polyoxyethylene hydrogenated castor oil (e.g. HCO-60).

As optional components, the routine thickener (e.g. carboxypolymethylene), coloring agent, sweetener, flavoring agent, diluent, etc. can be added.

Meanwhile, the process for producing the medicinal composition of this invention is as follows.

A liquid medicinal composition according to this invention can be produced by mixing an insoluble drug and two or more surfactants and stirring the mixture, for instance, in the routine manner to cause at least one of said two or more surfactants to dissolve said insoluble drug and the other surfactant or surfactants.

The amounts of various components of the medicinal composition of this invention are preferably set according to the species of each component to be used but may for example be as follows.

The effective amount or dosage of the insoluble drug varies with the patient's age, diagnosis and severity of illness, among other factors, but may usually be about 0.01~1000 mg, preferably 0.05~500 mg, more preferably 0.1~100 mg as active ingredient per day for therapeutic use and generally about 0.1 mg, 0.5 mg, 1 mg, 5 mg, 10 mg, 50 mg, 100 mg, 250 mg or 500 mg is administered per dose. The recommended proportion of the insoluble drug in the medicinal composition of this invention relative to the total amount of the composition is 0.01~20%, preferably 0.1~10%.

The recommended proportion of the surfactant or surfactants other than the surfactant capable of "dissolving the insoluble drug and the other surfactant or surfactants", among said two or more surfactants, relative to the total amount of the composition, is 0.1~80%, preferably 0.5~60% and more preferably 1~10%. The preferred formulating ratio (by weight) of the insoluble drug to the particular surfactant or surfactants is 1:0.5~100, more preferably 1:1~50 and most preferably 1:2~30.

The following examples are intended to illustrate this invention in further detail and should by no means be construed as defining the scope of the-invention.

EXAMPLE 1

| FK506 Substance | 1 mg |
| --- | --- |
| Polyethylene hydrogenated castor oil | 30 mg |
| Propylene glycol monocaprylate | q.s. |
| Total | 100 µl |

FK506 Substance and polyoxyethylene hydrogenated castor oil are mixed with propylene glycol monocaprylate and the mixture is stirred or otherwise treated in the routine manner for dissolving to provide a solution-form composition.

EXAMPLE 2

The following compositions are prepared by the same procedure as in Example 1.

(A)

| FK506 Substance | 125 mg |
| --- | --- |
| Polyoxyethylene hydrogenated castor oil | 1.5 g |
| Propylene glycol monocaprylate | q.s. |
| Total | 5 ml |

(B)

| FK506 Substance | 125 mg |
| --- | --- |
| Polyoxyethylene hydrogenated castor oil | 1.5 g |
| Propylene glycol dicaprylate | q.s. |
| Total | 5 ml |

EXAMPLE 3

Dissolution Test

The dissolution test was performed in accordance with Japanese Pharmacopoeia (J.P.), Method 2 (paddle method). Thus, the test solution is 500 ml of water and the paddle speed is 50 rpm. The composition A prepared in Example 2 is filled into a capsule shell (200 µl) and added to the test solution. At 5, 10, 15, 20, 30, 45 and 60 minutes thereafter, 0.5 ml of the test solution is sampled, mixed with an equal volume of methanol and subjected to analysis by high-performance liquid chromatography. The release rate of FK506 Substance from composition A as determined by the above procedure was T 50%=22.0±1.6 min (mean±standard error).

EFFECTS OF INVENTION

The medicinal composition of this invention was confirmed to be a composition expressing a high solubilizing performance and having good stability and workability, high absorption efficiency, and satisfactory oral absorbability with little variation.

In accordance with this invention, those compounds which, because of their poor solubility in water, were found to be not absorbed in a stable manner after oral administration so that the idea to develop them as pharmaceuticals had to be abandoned and the utility of which as drugs could not be fully exploited can now be provided in useful oral dosage forms.

The composition of the invention can be administered externally, parenterally and topically, e.g. by instillation into the eye or the nostrils, as well. For oral medication, the composition can be directly taken in the encapsulated form or dispersed in water, juice or the like in advance and taken in the solution form. For external application, it can be dispersed in water or the like in advance and applied in the form of a lotion. For parenteral medication, the composition is dispersed in water or saline and administered. For nasal application, it is dispersed in water or the like and instilled into the nostrils. For topical application as an ophthalmic preparation, it can be dispersed in water or an isotonic buffer in advance and instilled into the eye.

Furthermore, by judicious selection of the respective components, the rate of dissolution and/or rate of release of the drug can be freely controlled, that is to say a controlled release dosage form can be provided.

When the insoluble drug is said tricyclic compound (I), the medicinal composition of this invention can be used in the therapy and prophylaxis of the following diseases and conditions with advantage by exploiting the pharmacologic actions of the compound (I).

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

and infections caused by pathogenic microorganisms (e.g. Aspergillus fumigatus, Fusarium oxysporum, Trichophyton asteroides, etc.).

Furthermore, medicinal preparations of said tricyclic compound (I) are useful for the therapy and prophylaxis of the following diseases.

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca(dry eye) phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilicgastroenteritis, mastocytosis, Crohn—s disease and ulcerative colitis);

food-related allergic diseases with symptomatic manifestation remote from the gastrointestinal tract (e.g. migrain, rhinitis and eczema); renal diseases (e.g. intestitial nephritis, Goodpasture's syndrome, hemolytic uremic syndrome, and diabetic nephropathy);

nervous diseases (e.g. multiple myositis, Guillain-Barre syndrome, Meniere's disease, multiple neuritis, solitary neuritis, cerebral infarctions Alzheimer's diseases Parkinson's diseases amyotrophic lateral sclerosis (ALS) and radiculopathy);

cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy) ;

endocrine diseases (e.g. hyperthyroidism, and Basedow's disease);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g. osteoporosis);

respiratory diseases (e.g. sarcoidosis, pulmonary fibrosis, and idiopathic interstitial pneumonia);

skin diseases (e.g. dermatomyositis, leukoderma vulgaris, ichthyosis vulgaris, photosensitivity, and cutaneous T-cell lymphoma);

circulatory diseases (e.g. arteriosclerosis, atherosclerosis, aortitis syndrome, polyarteritis nodosa, and myocardosis);

collagen diseases (e.g. scleroderma, Wegener's granuloma, and Sjogren's syndrome);

adiposis;

eosinophilic fasciitis;

periodontal diseases (e.g. damage to gingiva, periodontium, alveolar bone or substantia ossea dentis);

nephrotic syndrome (e.g. glomerulonephritis);

male pattern alopecia, alopecia senile;

muscular dystrophy;

pyoderma and Sezary syndrome; chromosome abnormality-associated diseases (e.g.

Down's syndrome);

Addison's disease;

active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)):

intestinal diseases (e.g. endotoxin shock, pseudomembranous colitis, and drug- or radiation-induced colitis):

renal diseases (e.g. ischemic acute renal insufficiency, chronic renal failure):

pulmonary diseases (e.g. toxicosis caused by pulmonary oxygen or drugs (e.g. paracort, bleomycin, etc.), lung cancer, and pulmonary emphysema):

ocular diseases (e.g. cataracta, iron-storage disease (siderosis bulbi), retinitis, pigmentosa, senile plaques, vitreous scarring, corneal alkali burn):

dermatitis (e.g. erythema multiforme, linear immunoglobulin A bullous dermatitis, cement dermatitis):

and other diseases (e.g. gingivitis, periodontitis, sepsis, pancreatitis, and diseases caused by environmental pollution (e.g. air pollution), aging, carcinogen, metastasis of carcinoma, and hypobaropathy)];

diseases caused by histamine release or leukotriene C4 release;

restenosis of coronary artery following angioplasty and prevention of postsurgical adhesions;

Autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans),or polychondritis);

Human Immunodeficiency Virus (HIV) infections AIDS;

allergic conjunctivitis;

hypertrophic cicatrix and keloid due to trauma, burn, or surgery.

In addition, the tricyclic compound (I) has liver regenerating activity and/or activities of stimulating hypertrophy and hyperplasia of hepatocytes.

Therefore, the medicinal composition of the present invention is useful for the therapy and prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

And further, the present composition is useful for preventing or treating various diseases because of its useful pharmacological activity such as augmenting activity of chemotherapeutic effect, activity of cytomegalovirus infection, anti-inflammatory activity, inhibiting activity against peptidyl-prolyl isomerase or rotamase, antimalarial activity, antitumor activity, and so on.

The disclosure of the patents, patent applications and references cited herein in the present application is encompassed within the description of the present specification.

What is claimed is:

1. A medicinal composition comprising a tricylic compound (I) of the following general formula or a pharmaceutically acceptable salt thereof,

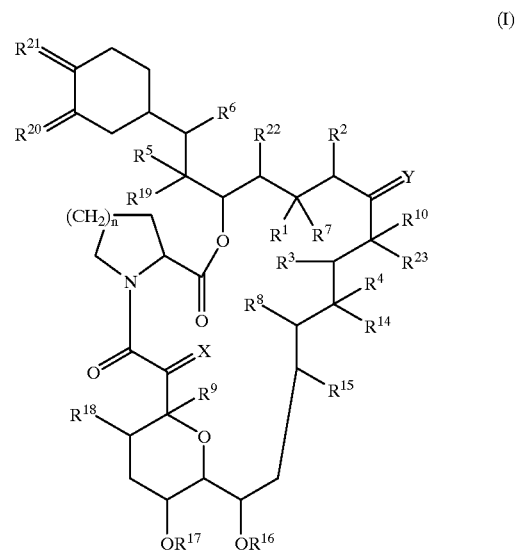

wherein each of adjacent pairs of $R^1$ and $R^2$, $R^3$ and $R^4$ or $R^5$ and $R^6$ independently
(a) is two adjacent hydrogen atoms, or
(b) may form another bond formed between the carbon atoms to which they are attached, and further, $R^2$ may be an alkyl group; $R^7$ is a hydrogen atom, a hydroxy group, a protected hydroxy group or an alkoxy group, or an oxo group together with $R^1$;
each of $R^8$ and $R^9$ is independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;
X is an oxo group, (a hydrogen atom and a hydroxy group), (a hydrogen atom and a hydrogen atom) or a group represented by the formula —$CH_2O$—;
Y is an oxo group, (a hydrogen atom and a hydroxy group), (a hydrogen atom and a hydrogen atom), or a group represented by the formula N—$NR^{11}R^{12}$ or N—$OR^{13}$;
each of $R^{11}$ and $R^{12}$ is independently a hydrogen atom, an alkyl group, an aryl group or a tosyl group;
each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;
each of $R^{20}$ and $R^{21}$ is independently an oxo group or ($R^{20}$a and a hydrogen atom) or ($R^{21}$a and a hydrogen atom) in which each of $R^{20}$a and $R^{21}$a is independently a hydroxy group, an alkoxy group or a group represented by the formula —$OCH_2OCH_2CH_2OCH_3$, or $R^{21}$a is a protected hydroxy group, or $R^{20}$a and $R^{21}$a may together represent an oxygen atom in an epoxide ring;
n is an integer of 1 or 2; and
in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl and a group of the formula —$CH_2Se(C_6H_5)$;

propylene glycol mono- or di-fatty acid ester; and polyoxyethylated hydrogenated castor oil.

2. The medicinal composition according to claim 1, wherein the tricyclic compound (I) is the one therein each of adjacent pairs of $R^3$ and $R^4$ or $R^5$ and $R^6$ independently may form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

each of $R^{20}$ and $R^{21}$ is independently ($R^{20}$a and a hydrogen atom) or ($R^{21}$a and a hydrogen atom) in which each of $R^{20}$a and $R^{21}$a is a hydroxy group or an alkoxy group, or $R^{21}$a is a protected hydroxy group; and n is an integer of 1 or 2.

3. The medicinal composition according to claim 2, wherein said tricyclic compound (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

4. The medicinal composition according to claim 1, wherein the propylene glycol mono- or di-fatty acid ester is propylene glycol monocaprylate or propylene glycol dicaprylate.

* * * * *